United States Patent [19]

Benton

[11] Patent Number: 5,152,882
[45] Date of Patent: Oct. 6, 1992

[54] INTEGRAL HYDROLYSIS LAYER JUNCTION

[75] Inventor: Barry W. Benton, Orange, Calif.

[73] Assignee: Rosemount Inc., Eden Prairie, Minn.

[21] Appl. No.: 589,936

[22] Filed: Sep. 28, 1990

[51] Int. Cl.$^5$ ............................................. G01N 27/26
[52] U.S. Cl. ..................................... 204/416; 204/435
[58] Field of Search ................ 204/435, 421, 416, 414

[56] References Cited

U.S. PATENT DOCUMENTS

| | | | |
|---|---|---|---|
| 3,250,688 | 5/1966 | Arthur | 204/414 |
| 3,575,834 | 4/1971 | Hoole | 204/416 |
| 4,002,547 | 1/1977 | Neti et al. | 204/195 F |
| 4,913,793 | 4/1990 | Leonard | 204/435 |
| 4,975,175 | 12/1990 | Karube | 204/414 |

Primary Examiner—John Niebling
Assistant Examiner—Bruce F. Bell
Attorney, Agent, or Firm—Kinney & Lange

[57] ABSTRACT

The present invention includes an ion diffusion junction in an electrochemical cell. The junction includes a polymer matrix that is impermeable to the sample solution. A plurality of inclusions are disposed within the junction matrix and oriented to form continuous hydrolytic pathways extending between the sample solution and the reference electrolyte such that ion diffusion occurs along the hydrolytic pathways.

9 Claims, 1 Drawing Sheet

INTEGRAL HYDROLYSIS LAYER JUNCTION

BACKGROUND OF THE INVENTION

The present invention relates generally to electrochemical cells, and in particular, it relates to the junction structure of electrochemical cells.

Ion concentrations of solutions are typically measured through the use of an ion sensing electrode in connection with a reference electrode or cell. The potential difference between the two electrodes is a function of the concentration of the ion in the solution being sensed. A common example is the measurement of pH in aqueous solutions in which a pair of electrodes is used to measure the hydrogen ion concentration and a pH meter provides the instrumentation that indicates the quantitative value.

Reference cells ordinarily include a salt solution disposed within a chamber, an electrode within the salt solution, and a junction which provides an ionic connection between the salt solution of the reference electrode and the solution being sampled.

The liquid junctions of the prior art reference electrodes have been constructed to permit leakage, that is fluid flow between the reference salt solution and the sampling solution. Such junctions have included agar gel connections, wicks, asbestos fibers, small capillary tubes, glass tubes with cracks therein, sintered glass plugs sealed in glass tubes, annular passages provided between solid metal rods and the walls of the tubes, porous ceramic rods, sintered plastic rods, and ground glass sleeves.

More recently, the Neti et al U.S. Pat. No. 4,002,547 describes the use of a relatively strong, electrochemically inactive salt distributed through a hydrophobic polymer. The salt is incorporated into the polymer prior to molding and thereafter the polymeric bar stock is sintered to form the reference electrode housing.

In an increasing number of applications, liquid flow or leakage between the reference solution and the sampling solution present problems. For example, care must be taken to minimize loss of the reference solution due to temperature or pressure extremes since such extremes will force the solution from the cell decreasing the life of the cell or destabilizing the cell. In addition, the reference cell can become contaminated by leakage of the sample solution into the cell. This leakage can cause dilution of the reference solution and/or can poison the cell.

In many applications, there are strict sanitary requirements which make the seals of the prior art reference electrodes unacceptable. Such sanitary requirements do not permit sealing mechanisms such as a typical 0-ring and groove that are found in prior art reference electrodes. In addition, prior art junctions which permit (leak) fluid into and out of the cell may compromise sanitary conditions.

Lastly, liquid junctions add greatly to the cell's costs due to the additional parts needed to form the junction and the labor involved in providing the junction.

SUMMARY OF THE INVENTION

The present invention includes an ion diffusion junction in an electrochemical cell. The junction includes a polymer matrix that is impermeable to the sample solution. A plurality of inclusions are disposed within the polymer matrix and oriented to form continuous hydrolytic pathways extending between the sample solution and the reference electrolyte such that ion diffusion occurs along the hydrolytic pathways.

In a preferred aspect of the present invention, the junction is an integral part of the cell housing. Being a fluid impermeable junction and being integral with the housing, eliminates the possibility of fluid leakage between the reference electrolyte and the sample solution.

DETAILED DESCRIPTION OF THE PREFERRED EMBODIMENTS

Figure 1:
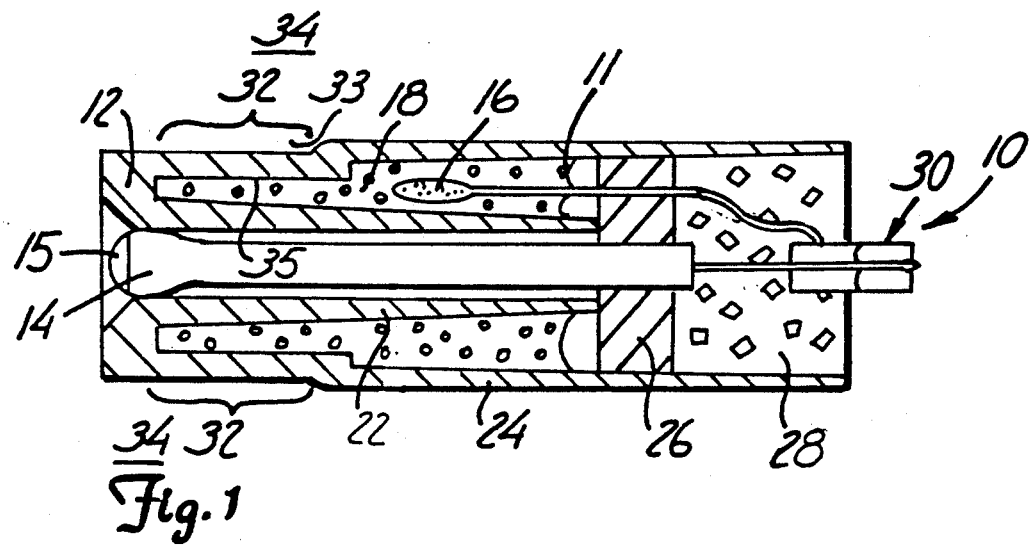
FIG. 1 is a sectional view of the electrochemical cell sensor of the present invention.

The present invention includes an electrochemical cell sensor 10 having a reference half cell 11 with an ion diffusion junction that is impermeable to fluid flow. In the preferred embodiment 10 illustrated in FIG. 1, the sensor 10 includes a housing 12, an indicator or ion measuring electrode 14, and the reference half cell 11.

The housing 12 may be made by any suitable means such as molding, casting, or extrusion. One preferred method of producing the housing 12 is injection molding. The housing may be made of a thermoplastic, a thermoset plastic, a rubber, a ceramic, or a glass. Although the preferred housing 12 is of a type that houses both the ion specific electrode 14 and the reference half cell 11, the present invention is also applicable to housings that include only the reference half cell.

The reference half cell 11 includes a electrode 16 disposed in an electrolyte 18 within the housing 12. Both the electrolyte 18 and the electrode 16 are preferably electrically insulated from the ion specific electrode 14 by an inner wall 22 that is generally cylindrical in configuration. Alternatively, the body of electrode 14 can be formed of an insulating glass to provide electrical insulation. The inner wall 22 encloses the ion specific electrode 14 except for an active region or distal portion 15, which is exposed to a sample solution 34. The housing 12 further includes an outer wall 24 that is also generally cylindrical in configuration forming the outer wall of the sensor 10. The outer surface of the inner wall 22 and the inner surface of the outer wall 24 form an enclosure that houses the electrode 16 and the electrolyte 18.

The sensor 10 is sealed by a suitable plug 26 and potting material 28 that are well known in the art. A connector 30 is used to connect both the ion specific electrode 14 and the electrode 16 to a suitable instrument (not shown) for indicating or recording the potential being sensed.

An ion diffusion junction 32 separates the electrolyte 18 from the sample solution 34 which is the solution of interest. The junction 32 includes a sample solution facing surface 33 and a reference electrolyte facing surface 35. The ion diffusion junction 32 of the present invention is impermeable to fluid flow and preferably an integral portion of the sensor housing 12. Being impermeable to fluid flow and being an integral portion of the sensor housing eliminates leakage problems that are associated with traditional junctions. In addition, since the junction is an integral part of the housing, the housing and the junction are made simultaneously decreasing production costs.

The junction 32 of the present invention includes a solid matrix in which a plurality of inclusions are disposed. By inclusions is meant any material, either hollow or solid having at least a solid surface. The material may be organic or inorganic and in the form of flakes, crystals, particles, beads, or fibers, or a mix of such materials. One preferred material for use as inclusions is glass fibers.

The junction is characterized by hydrolytic activity along the inclusions. By hydrolytic activity is meant that reaction (hydrolysis) which produces a weak base or a weak acid by reaction with water. The hydrolysis can occur along the interface between the matrix substance and the inclusion substance, or the inclusions may have hydrolyzable surface layers, or a hydrolyzable coating may be applied to the inclusions, or a combination of any of the above.

The hydrolytic activity is necessary for ion diffusion to occur along an interface or interfaces between the inclusions and the matrix. The inclusions are oriented to form continuous ion diffusion pathways within the matrix from a surface of the junction facing the electrolyte 18 to an opposing surface of the junction facing the sampling solution 34. The ion diffusion pathways are not porous in the common sense of the word. The ion diffusion pathways permit the transfer of ions along the pathways by diffusion. If a pore size equivalent were to be estimated, it is believed that the equivalent would be less than 0.025 microns.

Preferably, the matrix and inclusions are made of inert materials such that when the inclusions and the matrix are exposed to the aqueous sample solution, hydrolysis occurs along the interface surfaces between the matrix and the inclusions. A hydrolyzable coating is preferably applied to the inclusions to provide enhanced hydrolysis. Since the junction matrix material and the inclusions are in contact with both the sample solution and the reference electrolyte, the material chosen for the inclusion and the junction matrix material must be "inert", that is electrically insulative, and not having chemical reactions which would produce interfering potentials.

The junction matrix is preferably made of the same material as the housing thereby making the junction integral with the housing. The junction material may be a thermoplastic, a thermoset plastic, a liquid crystal, a rubber, a ceramic, a glass, or a combination of such materials. Preferably, the junction matrix is a thermoplastic.

One method of producing continuous ion diffusion pathways within the junction 32 is by injection molding the sensor housing 12 using glass fibers as inclusions interspersed within the thermoplastic. A preferred material is part number 107Z with 1% titanium dioxide as a white colorant prepared by RTP Company of Winona, Minn. USA. Sizing is preferably included, which may include starch-like materials, silanes and the like. Sizing is coated on to the glass fibers as a hydrolyzable layer prior to molding.

In order for the ion diffusion pathways to act as such, the pathways must be contiguous from the sample solution to the reference electrolyte. In the case of glass fibers, if the wall thickness of the junction exceeds the length of the fiber, the ion diffusion rate may be very low, and possibly so low that the junction is unusable. In the case where the molded design in an injection molding process tends to align the glass fibers with the polymer melt flow, few of the glass fibers will be oriented transverse to the melt flow and available as such to form ion diffusion pathways across the junction. In either case, the wall of the junction must then be reduced to a selected fraction of the length of the glass fibers.

Alternatively, the mold can be designed to produce disordered flow regions disordering the fibers in the area of the housing which is intended for the junction. Some percentage of the fibers will become oriented transversely to the melt flow so that contiguous ion diffusion pathways are formed across the wall of the housing in the area of the junction.

Figure 2:
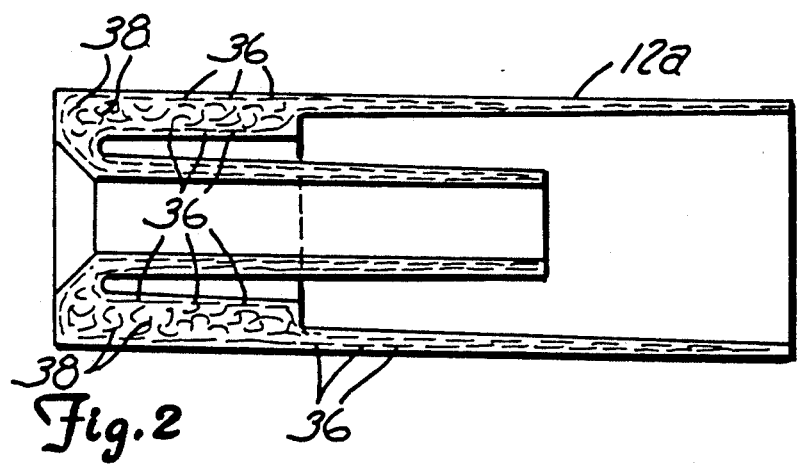
FIG. 2 is a sectional view of the cell housing of the cell sensor of the present invention prior to machining.

As illustrated in FIG. 2, a housing 12a shown in cross section indicates ordered flow regions which include oriented fibers 36 and a disordered flow region which includes randomly dispersed fibers 38. The fibers 36 are oriented in an orderly fashion near the surfaces of the housing 12a. The randomly dispersed fibers 38 have a portion of their population which is transverse to the direction of the melt flow and which extend between opposing flow regions. The fibers 38 constitute the ion diffusion pathways.

The transverse fibers 38 must be exposed so that hydrolysis can occur to form the ion diffusion pathways between the matrix and the inclusions. The ordered flow regions are removed to the extent needed to expose the fibers to the surface.

Figure 3:
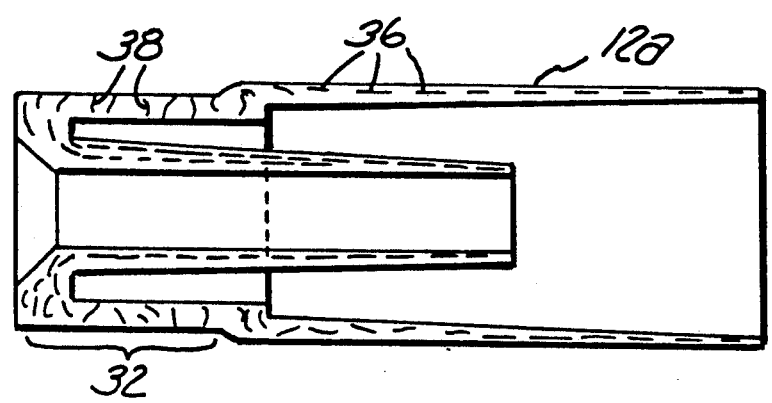
FIG. 3 is a sectional view of the housing of the cell sensor of the present invention after machining.

A number of methods may be used to expose the transversely oriented fibers 38, depending on the matrix material. These methods for removing of the matrix material include chemical, thermal, ionic, electrical, plasma, or mechanical methods. In the example discussed wherein the matrix material is a thermoplastic and the inclusions are glass fibers, a machining operation is presently preferred to produce the junction 32 as illustrated in FIG. 3.

The diffusion properties of the junction 32 are controlled by adjusting any one or combination of a number of parameters including surface area of the junction, length of the glass fibers, the depth of removal of the ordered flow region, the thickness of the junction, and the extent of fiber orientation.

With regard to surface area of the junction, the diffusion rate can be controlled by the amount of surface area that is exposed by machining or other operation. Along the areas of the housing in which the ordered flow region is not removed, the oriented fibers 36 remain along with the thermoplastic skin formed during the molding process, making ion diffusion through such areas negligible.

The fiber length can also be varied to increase or decrease ion diffusion rate since each fiber and/or each chain of intimate fibers contiguous between the sample solution and the electrolyte defines a hydrolyzed ion diffusion pathway. If the fiber length is increased, the diffusion rate is increased. Decreasing the fiber length will decrease the number of fibers which form continuous pathways from the electrolyte surface to sample solution surface thereby decreasing the diffusion rate.

As discussed previously, the parameters of the molding process can also be controlled in a known manner to minimize or maximize the ordered flow region thereby increasing or decreasing the number of fibers that become transversely orientated in the matrix. The ordered flow regions can be seen as regions which tend to have more laminar flow during molding and the disordered regions can be seen as regions which tend to have more turbulent flow during molding.

Ion diffusion can also be controlled by increasing or decreasing the wall thickness of the junction area thereby increasing or decreasing the number of fibers that form pathways between the reference solution surface and the sample solution surface.

The composition of the material at the junction may also be changed to increase or decrease the number of ion diffusion pathways. For example, increasing the fiber content of the junction relative to the amount of matrix material will increase the number of ion diffusion pathways, and therefore increase the diffusion rate. Similarly, the inclusion material and the matrix material may be selected for ease of hydrolysis to occur. The more hydrolyzable the ion diffusion pathways are, the less resistant such materials are to ion diffusion, increasing ion diffusion. In addition, the interface between the inclusions and the matrix may be made more hydrolyzable by coating the inclusions prior to molding with the hydrolyzable coating.

Due to the unique ion diffusion pathways of the present invention junction, the junction wall can be made thicker thereby decreasing costs and increasing the structural integrity of the junction. For example, in one working embodiment, the junction wall has been as thick as 0.12 inches which is four times the thickness of commonly used prior art junctions.

In addition, the junction of the present invention requires no boiling or pressurizing to activate the junction, as many prior art junctions require.

The electrolyte 18, as illustrated in FIG. 1, is a solid electrolyte having a solid electrolyte matrix of bound salt granules and a hydrophilic, long chain polymer. The electrolytic salt is immobilized within a binder and the hydrophilic polymer chains provide a mechanism for ion diffusion through the solid. A high boiling point alcohol is also added to enhance solvation of the salt in the presence of uncured epoxy components, which enhances both initial wetting and rewetting after the probe has been exposed to air. A minimum amount of water is incorporated to hydrate the electrolyte and the junction 32. In a preferred embodiment, the solid electrolyte 18 is used with the junction 32. However, it is within the scope of the present invention to use the junction 32 with prior art electrolytes, and conversely, using the solid electrolyte of the present invention with conventional liquid junctions.

The electrolyte matrix may be made of any type of adhesive or cohesive insulating material such as epoxy, cyanoacrylates, silicones, urethanes, ceramics, and waxes. Preferably, the binder is a two-part epoxy such as TRA-BOND F-117 resin & hardener in the chemical families Bis-A Epichlorohydrin Epoxide Reaction Product and Aliphatic Amine Mixture, respectively, from Tra-con, Inc. of Medford, Mass., USA. The binder immobilizes the salt.

The salt used is a strong electrolyte and can be any conventional salt normally used in solution in a reference half cell, such as potassium chloride. Salt in the electrolyte of the present invention is in solid form such as crystal, grain, granules, or powder. In the embodiment discussed, salt granules are preferred.

The hydrophilic polymer is a high molecular weight (2 million to 50 million) polymer that is both hydrophilic and pseudoplastic. By pseudoplastic is meant that the viscosity of the material is inversely proportional to the amount of shear that the material is exposed to. The hydrophilic polymer also must have the ability to reform polymer chains after mixing, but before the mixture cures to form a network of polymer chains within the solid electrolyte. Such a characteristic is advantageous for preparing the mixture to form the electrolyte 18. If the mixture is blended in a high shear environment and the hydrophilic polymer chains are broken due to the shear, the polymer needs to have the ability to reform upon cessation of the blending. The hydrophilic polymer thusly forms a network within the binder upon curing. It is along such network that ion diffusion is believed to occur. Preferably, the polymer is a natural biopolysaccharide. One such preferred polysaccharide is xanthan gum from the Kelco division of Merck & Co. Inc..

A high boiling point solvent such as glycerol is added to the binder/salt mixture to provide the salt with some solubility. The high boiling point solvent is also miscible in water and the sample solution. The solvent should have a boiling point that is suitable for the particular application temperature in which the reference half cell will be used. Glycerol and other high boiling point alcohols are within the scope of the present invention.

The wetting agent provides a mechanism to enhance ion transfer from the electrode 16 to the electrolyte 18, and from the junction 32 to the electrolyte 18. One suitable wetting agent is Tergitol Non-ionic surfactant 15-S-9 from Union Carbide Corporation of Danbury Conn. USA.

The cell of the present invention needs only a very limited water content, such as that available from Ultra High Viscosity Double Junction Gel Part Number 7921003 from Rosemount Analytical Inc. of Irvine, Calif., USA, since the water is bound in the solid electrolyte matrix and is not easily lost through the junction.

The cell of the present invention also has an excess amount of salt within the electrolyte binder which is immobilized due to the solid nature of the binder. The immobility of the salt reduces ion mobility. In addition, the low concentration of the polymer network formed by the hydrophilic polymer minimizes ion diffusion. All of the above make ion concentration at the electrode very stable.

The present invention's reduced ion mobility inhibits poisoning by sample solution ion diffusion, protecting the electrode and increasing cell life.

The present invention also eliminates the problem of excess salt build-up along the junction since the excess salt is immobilized in the electrolyte binder. In addition, since the electrolyte is immobilized, the electrolyte cannot move across the junction leaving primarily sample solution within the junction with little or no pressure change error resulting therefrom.

The following example is intended to be purely exemplary and not intended to limit the present invention in any way. All concentrations are by weight, except where noted.

EXAMPLE

A solid electrolyte for use in a reference half cell was made of one part freshly mixed epoxy such as Tra-bond F117 and three parts by weight potassium chloride granules (KCl) with diameters in the range of 0.015 to 0.030 inches. The epoxy/potassium chloride mixture is thoroughly stirred to coat all of the potassium chloride granules with the epoxy until a course putty type consistency is achieved. One-half part of a saturated KCl 2 percent by weight xanthan gum gel was added to the uncured epoxy/KCl mixture. Even smaller amounts, approximately 1.7% by weight each of both glycerol and Tergitol are added to enhance solvation of the KCl and wetting of the electrode/electrolyte and electrolyte/junction interfaces.

The mixture was then whipped into a creamy paste and placed within the electrode housing 12 with the electrode 16 positioned within the electrolyte mixture. The electrolyte was then permitted to cure. The electrode 16 was an Ag/AgCl electrode. The cell 11 of the present invention performed similarly to a standard liquid filled reference half cell.

Although the present invention has been described with reference to preferred embodiments, workers skilled in the art will recognize that changes may be made in form and detail without departing from the spirit and scope of the invention.

What is claimed is:

1. A junction in an electrochemical cell, the junction having a sample solution facing surface and a reference electrolyte facing surface, the junction comprising:
   a polymer matrix impermeable to the sample solution;
   a plurality of inclusions disposed withinthe matrix and oriented to form continuous hydrolytic ion diffusion pathways extending between the sample solution facing surface and the electrolyte facing surface such taht ion diffusion occurs along the pathways without flow of the sample solution along the pathways; and
   a hydrolyzable layer between the inclusions and the matrix.

2. The junction of claim 1 wherein the polymer matrix is a thermoplastic.

3. The junction of claim 1 wherein the inclusions are glass fibers.

4. The junction of claim 1 wherein the hydrolyzable coating is a silane.

5. An electrochemical cell sensor housing, the cell comprising:
   a liquid impermeable housing wall defining a reference electrolyte enclosure;
   an electrolyte disposed within the electrolyte enclosure;
   an electrode in conductive relationship with the electrolyte;
   a junction disposed within the housing wall, the junction comprising a polymer matrix having a plurality of inclusions disposed therein and a hydrolyzable layer between the inclusions and the matrix and the inclusions oriented to form continuous hydrolytic ion diffusion pathways that are in conductive relationship with the electrolyte and with a sample solution without flow of the sample solution along the pathways.

6. The cell of claim 5 wherein the wall is made of a thermoplastic.

7. The cell of claim 5 wherein the inclusions are glass fibers.

8. The cell of claim 5 wherein the hydrolyzable coating is a starch-like material.

9. The cell of claim 5 wherein the housing wall and the junction are integrally formed by injection molding.

* * * * *

UNITED STATES PATENT AND TRADEMARK OFFICE
CERTIFICATE OF CORRECTION

PATENT NO. : 5,152,882

DATED : October 6, 1992

INVENTOR(S) : BARRY W. BENTON

It is certified that error appears in the above-identified patent and that said Letters Patent is hereby corrected as shown below:

Title page, item [56], insert the followings:

| | | | |
|---|---|---|---|
| 3,590,810 | 7/1971 | Kopecky | 128/2.06 |
| 3,843,506 | 10/1974 | Jerrold-Jones | 204/195F |
| 4,020,235 | 4/1977 | Giuffre et al | 428/443 |
| 4,021,327 | 5/1977 | Grot | 204/296 |
| 4,052,285 | 10/1977 | Dobson | 204/195 |
| 4,132,819 | 1/1979 | Giuffre et al | 427/341 |
| 4,233,257 | 11/1980 | Maruyama et al | 264/113 |
| 4,270,996 | 6/1981 | Suhara et al | 204/98 |
| 4,360,601 | 11/1982 | Copeland et al | 521/27 |
| 4,431,508 | 2/1984 | Brown, Jr | 204/418 |
| 4,507,194 | 3/1985 | Shimomura et al | 204/435 |
| 4,519,973 | 5/1985 | Cahalan et al | 264/267 |

Col. 7, line 24, delete "withinthe", insert "within the"

Col. 7, line 28, delete "taht", insert "that"

Col. 6, line 67, delete "course", insert "coarse"

Signed and Sealed this

Nineteenth Day of October, 1993

Attest:

BRUCE LEHMAN

Attesting Officer

Commissioner of Patents and Trademarks